US010918677B2

(12) United States Patent
Mandelboim et al.

(10) Patent No.: US 10,918,677 B2
(45) Date of Patent: Feb. 16, 2021

(54) **ATTENUATED OR INACTIVATED PATHOGENIC *ESCHERICHIA COLI* FOR TREATING UROGENITAL CANCER**

(71) Applicants: YISSUM RESEARCH DEVELOPMENT COMPANY OF THE HEBREW UNIVERSITY OF JERUSALEM LTD., Jerusalem (IL); HADASIT MEDICAL RESEARCH SERVICES AND DEVELOPMENT LTD., Jerusalem (IL)

(72) Inventors: Ofer Mandelboim, Shoham (IL); Gilad Benjamin Bachrach, Moshav Beit Zait (IL); Chamutal Gur, Jerusalem (IL); Vladimir Yutkin, Rehovot (IL)

(73) Assignees: YISSUM RESEARCH DEVELOPMENT COMPANY OF THE HEBREW UNIVERSITY OF JERUSALEM LTD., Jerusalem (IL); HADASIT MEDICAL RESEARCH SERVICES AND DEVELOPMENT LTD., Jerusalem (IL)

( * ) Notice: Subject to any disclaimer, the term of this patent is extended or adjusted under 35 U.S.C. 154(b) by 18 days.

(21) Appl. No.: 15/525,094

(22) PCT Filed: Nov. 10, 2015

(86) PCT No.: PCT/IL2015/051085
§ 371 (c)(1),
(2) Date: May 8, 2017

(87) PCT Pub. No.: WO2016/075687
PCT Pub. Date: May 19, 2016

(65) Prior Publication Data
US 2018/0333439 A1 Nov. 22, 2018

Related U.S. Application Data

(60) Provisional application No. 62/077,483, filed on Nov. 10, 2014, provisional application No. 62/088,747, filed on Dec. 8, 2014.

(51) Int. Cl.
*A61K 35/74* (2015.01)
*A61P 35/00* (2006.01)
*A61K 9/00* (2006.01)
*C07K 14/245* (2006.01)
*C12N 1/36* (2006.01)
*A61K 39/39* (2006.01)
*A61K 39/00* (2006.01)

(52) U.S. Cl.
CPC ............ *A61K 35/74* (2013.01); *A61K 9/0034* (2013.01); *A61K 39/39* (2013.01); *A61P 35/00* (2018.01); *C07K 14/245* (2013.01); *C12N 1/36* (2013.01); *A61K 2039/521* (2013.01); *A61K 2039/54* (2013.01); *A61K 2039/55594* (2013.01)

(58) Field of Classification Search
None
See application file for complete search history.

(56) References Cited

U.S. PATENT DOCUMENTS

| | | | |
|---|---|---|---|
| 7,452,531 B2 * | 11/2008 | Bermudes | A61K 31/337 424/93.2 |
| 8,034,359 B2 | 10/2011 | Gunn | |
| 8,501,198 B2 | 8/2013 | Gunn | |
| 8,980,279 B2 | 3/2015 | Gunn | |
| 9,107,864 B2 | 8/2015 | Gunn | |
| 9,320,787 B2 | 4/2016 | Gunn | |
| 2007/0104733 A1* | 5/2007 | Gunn | A61K 35/74 424/204.1 |
| 2009/0324633 A1* | 12/2009 | Pizza | C07K 14/245 424/190.1 |
| 2012/0258135 A1* | 10/2012 | Gunn | A61K 39/0275 424/206.1 |
| 2013/0337012 A1 | 12/2013 | Gunn | |

FOREIGN PATENT DOCUMENTS

| | | |
|---|---|---|
| EP | 1765391 | 3/2007 |
| EP | 2085466 | 8/2009 |
| EP | 2286832 | 2/2011 |
| WO | 2005120560 | 12/2005 |

OTHER PUBLICATIONS

Moriel et al. Current Pharmaceutical Biotechnology, 2013, 14, 967-974.*
Intravesical BCG (Bacillus Calmette-Guerin vaccine for immunotherapy) https://www.myvmc.com/treatments/intravesical-bcg-bacillus-calmette-guerin-vaccine-for-innnnunotherapy/ retrieved Dec. 4, 2018.*
Mondul et al. Cancer Res. Nov. 15, 2010; 70(22):9218-9223.*
Babjuk et al., (2011) EAU guidelines on non-muscle-invasive urothelial carcinoma of the bladder, the 2011 update. European urology, 59(6), 997-1008.
Bachrach et al., (2000) A new single-copy mycobacterial plasmid, pMF1, from Mycobacterium fortuitum which is compatible with the pAL5000 replicon. Microbiology, 146(2), 297-303.
Bagley et al., (1983) Bacterial adherence to bladder tumors in the mouse. Journal of surgical oncology, 23(4), 236-238.
Bahar et al., (2009) Type IV pili are required for virulence, twitching motility, and biofilm formation of *Acidovorax avenae* subsp. *citrulli*. Molecular plant-microbe interactions, 22(8), 909-920.
Brandau et al., (2001) NK cells are essential for effective BCG immunotherapy. International journal of cancer, 92(5), 697-702.
Brausi et al., (2014) Side effects of Bacillus Calmette-Guerin (BCG) in the treatment of intermediate-and high-risk Ta, T1 papillary carcinoma of the bladder: results of the EORTC genito-urinary cancers group randomised phase 3 study comparing one-third dose with full dose and 1 year with 3 years of maintenance BCG. European urology, 65(1), 69-76.

(Continued)

*Primary Examiner* — Oluwatosin A Ogunbiyi
(74) *Attorney, Agent, or Firm* — Rothwell, Figg, Ernst & Manbeck, P.C.

(57) ABSTRACT

The present invention provides attenuated or inactivated pathogenic bacteria having anti-cancer properties, compositions comprising the bacteria, and use thereof for treating cancers of the urogenital system.

11 Claims, 11 Drawing Sheets

(56) References Cited

OTHER PUBLICATIONS

Chaushu et al., (2012) Direct recognition of Fusobacterium nucleatum by the NK cell natural cytotoxicity receptor NKp46 aggravates periodontal disease. PLoS Pathog, 8(3), e1002601; 12 pages.

Coley, (1910) The Treatment of Inoperable Sarcoma by Bacterial Toxins (the Mixed Toxins of the Streptococcus erysipelas and the Bacillus prodigiosus). Proceedings of the Royal Society of Medicine, 3(Surg_Sect), 1-48.

Ferlay et al., (2010) Estimates of cancer incidence and mortality in Europe in 2008. European journal of cancer, 46(4), 765-781.

Grange et al., (2008) The use of mycobacterial adjuvant-based agents for immunotherapy of cancer. Vaccine, 26(39), 4984-4990.

Günther et al., (1999) Optimizing syngeneic orthotopic murine bladder cancer (MB49). Cancer research, 59(12), 2834-2837.

Gur et al., (2013) Natural killer cell-mediated host defense against uropathogenic *E. coli* is counteracted by bacterial hemolysinA-dependent killing of NK cells. Cell host & microbe, 14(6), 664-674.

Herr, (2012) Intravesical bacillus Calmette-Guérin outcomes in patients with bladder cancer and asymptomatic bacteriuria. The Journal of urology, 187(2), 435-437.

Ingersoll & Albert, (2013) From infection to immunotherapy: host immune responses to bacteria at the bladder mucosa. Mucosal immunology, 6(6), 1041-1053.

Lane et al., (2007) Complex interplay between type 1 fimbrial expression and flagellum-mediated motility of uropathogenic *Escherichia coli*. Journal of bacteriology, 189(15), 5523-5533.

Miyazaki et al., (2013) Adverse reactions related to treatment compliance during BCG maintenance therapy for non-muscle-invasive bladder cancer. Japanese journal of clinical oncology, 43(8), 827-834.

Mobley et al., (1990) Pyelonephritogenic *Escherichia coli* and killing of cultured human renal proximal tubular epithelial cells: role of hemolysin in some strains. Infection and immunity, 58(5), 1281-1289.

Nielsen et al., (2014) Trends in stage-specific incidence rates for urothelial carcinoma of the bladder in the United States: 1988 to 2006. Cancer, 120(1), 86-95.

Radford et al., (2002) A recombinant *E. coli* vaccine to promote MHC class I-dependent antigen presentation: application to cancer immunotherapy. Gene therapy, 9(21), 1455.

Siegel et al., (2012) Cancer statistics for hispanics/latinos, 2012. CA: a cancer journal for clinicians, 62(5), 283-298.

Yarkoni & Rapp, (1980) Immunotherapy of experimental cancer by intralesional injection of emulsified nonliving mycobacteria: comparison of Mycobacterium bovis (BCG), Mycobacterium phlei, and Mycobacterium smegmatis. Infection and immunity, 28(3), 887-892.

Young et al., (2004) Cytokine-modified Mycobacterium smegmatis as a novel anticancer immunotherapy. International journal of cancer, 112(4), 653-660.

Yutkin et al., (2007) The expression level of ligands for natural killer cell receptors predicts response to bacillus Calmette-Guerin therapy: a pilot study. The Journal of urology, 178(6), 2660-2664.

Emergency disposal of public health emergency in the airport. Professional Emergency Rescue Committee of China Civil Airport Association, Beijing: China. Civil Aviation Publishing House 2013. p. 124 with machine translation.

* cited by examiner

Day 27

PBS

BCG

C93

ATTENUATED OR INACTIVATED PATHOGENIC *ESCHERICHIA COLI* FOR TREATING UROGENITAL CANCER

CROSS-REFERENCE TO RELATED APPLICATIONS

The present application is a national stage filing under 35 U.S.C. § 371 of PCT/IL2015/051085, filed on Nov. 10, 2015, and claims the benefit of priority to U.S. Provisional Application Nos. 62/077,483, filed Nov. 10, 2014 and 62/088,747, filed Dec. 8, 2014. Each application is incorporated herein by reference in its entirety.

FIELD OF THE INVENTION

The present invention relates to inactivated or attenuated pathogenic bacteria, compositions comprising the bacteria, and use thereof for treating cancers such as urinary and prostate cancers.

BACKGROUND OF THE INVENTION

Bladder cancer is the fourth most common cancer in men both in Europe and USA. The high and rising incidence rates in patients over 65 years suggest that the burden of this cancer will increase with population aging.

Use of bacteria to enhance immunity and treat cancer was pioneered in 1891 by William Coley, who successfully treated sarcomas with extracts of pyogenic bacteria (Coley, W. B. 1910, Proc R Soc Med. 3, 1-48).

The *Mycobacterium bovis Bacillus* Calmette-Guérin (BCG) vaccine is a standard treatment for superficial bladder cancer together with chemotherapy. BCG-induced tumor elimination involves a local immune response with massive release of cytokines and a delayed type immune response predominantly through Th1 cells.

Natural Killer (NK) cells are cells of the innate immune system that kill tumor and viral-infected cells Killing by NK cells is mediated mainly through the Natural Cytotoxic Receptors (NCRs) which recognize ligands present on the surface of target cells. The expression levels of the NCR ligands on bladder tumors can predict the effectiveness of BCG treatment on bladder cancer in humans (Yutkin et al. J Urol 178, 2660-2664). In a murine model, successful BCG treatment of bladder tumor was found to be NK-cells dependent and was completely ineffective in NK-deficient mice (Brandau et al., Int J Cancer 2001, 92, 697-702). BCG therapy for non-muscle invasive bladder cancer reduces the risk of recurrence by 32% and the odds of tumor progression by 27%. However, immunotherapy with BCG is greatly hampered by its toxicity and severe adverse reactions that result in discontinuous treatment in 10-58% of the patients. Though attenuated, BCG is still a virulent microbe and its inoculation in the patient's bladder often leads to serious life threatening infections. BCG can infect the lungs, liver, bone, and the circulatory system. This infection is hard to treat due to the slow response of BCG to antibiotics. In addition, BCG is a tedious (high maintenance), slow growing microbe (doubling time of 23 h).

Urinary tract infection (UTI), caused by urinary pathogenic *Escherichia coli* (UPEC) is a very common disease and approximately 50% of women will have at least one episode of UTI at some point of their lives. Natural Killer (NK) cells recognize various pathogens, however, their involvement in UPEC-mediated UTI is practically unknown. Lately, the inventors of the present invention showed that UPEC adhere to NK cells primarily via their type I fimbriae and kill NK cells by the hemolysinA toxin. In the absence of hemolysinA, NK cells directly respond to the bacteria and secrete TNF-α which results in reduction of bacterial burden in the infected bladders (Gur et al., 2013. Cell Host Microbe 14, 664-674).

WO 2005/120560 discloses methods of treating cancers of a specific organ, tissue or cell in a subject by administering an antigen of one or more pathogenic bacterial species that are pathogenic in the specific organ, tissue or cell.

EP Pat. No. 1765391 discloses a preparation of killed bacteria of one or more pathogenic bacterial species, or a cell wall extract, a cell membrane extract, a whole cell extract, or an isolated antigen thereof for use in treating a cancer in a specific organ or tissue in a subject.

Radford et al. (Gene Therapy, 2002, 9:1455-1463) describes that immunization of mice by direct injection of recombinant *E. coli* expressing listeriolysin O (tumor antigen) and ovalbumin (OVA) provides an anti-tumor response, resulting in complete protection of 75% of mice which are challenged with OVA-expressing melanoma cell line (B16-OVA).

There is an unmet need for additional approaches with improved effectiveness for treating cancer, having fewer or no side effects.

SUMMARY OF THE INVENTION

The present invention is directed to specific types of *E. coli* bacteria for treating urogenital cancer. The present invention in some embodiments provides mutated hemolysin deficient bacterial strains derived from urinary pathogenic *Escherichia coli* and compositions comprising same for treating cancer. The present invention in some embodiments further provides inactivated urinary pathogenic *E. coli* for treating cancer. In particular, the bacteria disclosed herein are useful for attenuating or inhibiting tumor growth and even inducing tumor regression. The present invention further provides methods of treating cancer that comprise administering mutated or inactivated pathogenic *E. coli* directly to the site of the tumor.

The present invention is based in part on the unexpected discovery that treating bladder tumor bearing mice with hemolysin mutated *E. coli* strains significantly improves the survival of the mice. In addition, pathogenic *E. coli* bacterial strains that were inactivated by formaldehyde showed highly potent anti-bladder cancer activity. Furthermore, the bacterial strains of *E. coli* when directly administered into the bladder, showed greatly superior anti-cancer activity when compared to *Mycobacterium bovis Bacillus* Calmette-Guérin (BCG) and *Helicobacter pylori*. It is now disclosed that treatment with bacteria according to the principles of the invention markedly reduced the tumor burdens in mice bearing bladder cancer. Unexpectedly, although the treatments started after the mice already had visible tumors, the tumors regressed and, remarkably, most tumors were eliminated within several weeks.

Without being bound by any particular theory or mechanism of action, the anti-cancer effect of the hemolysin deficient bacteria may be due to decreased cytotoxicity towards NK cells. Urinary pathogenic *Escherichia coli*, when inoculated into the bladder recruit natural killer cells to the bladder, adhere to the NK cells and kill them. When administered into the bladder, the hemolysin deficient bacteria of the invention recruit the NK (and T cells) to the bladder but do not kill, or kill with less efficiency, the NK cells. It is now disclosed for the first time that a mutation in the hemolysin gene hlyA is sufficient for eliciting an improved anti-cancer activity of uropathogenic *E. coli* (UPEC) harboring the mutation.

The present invention further discloses that strains of uropathogenic *E. coli* (UPEC), and enteropathogenic *E. coli* (EPEC) inactivated by formaldehyde, exhibits a highly potent anti-bladder cancer activity. Unexpectedly, the formaldehyde inactivated UPEC and EPEC had highly efficient anti-cancer effect on mice bearing visible and large tumors. The survival rate of these mice was remarkably high.

The present invention further provides advantageous methods of treating cancer comprising intravesicular administration of bacteria. The therapeutic activity of the bacteria was highly potent when administered directly into the bladder of mouse models of bladder cancer.

According to one aspect, the present invention provides a mutant hemolysin deficient bacterial strain derived from a pathogenic strain of *E. coli* or component thereof for use in treating a cancer of the genitourinary system.

According to some embodiments, the hemolysin deficient bacterial strain is a urinary or enteropathogenic mutated strain of *E. coli*. According to certain embodiments, the mutated bacterial strain is derived from uropathogenic *E. coli* (UPEC). According to other embodiments, the mutated bacterial strain is derived from enteropathogenic *E. coli* (EPEC).

According to some embodiments, the mutant hemolysin deficient *E. coli* bacterial strain or a component thereof is for use in treating urogenitary cancer by intravesicular administration. According to exemplary embodiments, the hemolysin deficient bacterial strain or component thereof is for local administration at or in proximity to the cancer site.

According to some embodiments, the mutated bacterial strain has a mutation in the hly gene.

According to some embodiments, the hly gene is selected from the group consisting of: hlyA, hlyC, and hlyD. Each possibility represents a separate embodiment of the invention.

According to some embodiments, the mutant hemolysin deficient bacterial strain has a reduced amount of hemolysin by at least 30%, 40%, 50%, 60%, 70%, 80%, 90%, or 95% compared to the wild type. Each possibility represents a separate embodiment of the invention.

According to some embodiments, the mutant hemolysin deficient bacterial strain has hemolysin having reduced activity by at least 25%, 30%, 40%, 50%, 60%, 70%, 80%, or 90% compared to the wild type. Each possibility represents a separate embodiment of the invention.

According to some embodiments, the mutant hemolysin deficient bacterial strain is attenuated.

According to additional aspect, the present invention provides an inactivated uropathogenic *Escherichia coli* strain CFT073 or component thereof for use in treating a cancer of the genitourinary system. According to some embodiments, the treating comprises intravesicular administration.

According to additional aspect, the present invention provides an inactivated pathogenic bacterial strain of *E. coli* or a component thereof for use in treating urogenitary cancer by intravesicular administration. According to exemplary embodiments, the inactivated pathogenic bacterial strain or component thereof is for local administration at or in proximity to the cancer site.

According to some embodiments, the inactivated pathogenic bacterial strain is uropathogenic *E. coli* (UPEC). According to other embodiments, the inactivated pathogenic bacterial strain is enteropathogenic *E. coli* (EPEC).

According to additional aspect, the present invention provides an *E. coli* bacterial strain for use in treating a cancer of the genitourinary system, wherein the bacterial strain has type I fimbria, the bacterial strain is selected from the group consisting of: (i) a mutant hemolysin deficient bacterial strain derived from a pathogenic strain of *E. coli*; (ii) an inactivated UPEC; and (iii) an inactivated EPEC. Each possibility represents a separate embodiment of the invention.

According to some embodiments, the UPEC strain is CFT073.

According to additional aspect, the present invention provides an *E. coli* bacterial strain for use in treating a cancer of the genitourinary system, wherein the bacterial strain overexpresses type I fimbria.

According to some embodiments, the cancer of the genitourinary system is selected from the group consisting of: bladder cancer, prostate cancer, kidney cancer and urethral cancer. Each possibility represents a separate embodiment of the invention. According to certain embodiments, the cancer of the genitourinary system is a bladder cancer. According to additional exemplary embodiments, the cancer is non-muscle-invasive urothelial carcinoma of the bladder.

According to some embodiments, the bacterial component is selected from the group consisting of a protein, a membrane and a cell wall fraction. Each possibility represents a separate embodiment of the invention. According to certain embodiments, the component is Type 1 fimbria. According to other embodiments, the component comprises Lipopolysaccharides (LPS).

According to some embodiments, the bacterial strain has type I fimbria.

According to some embodiments, the bacterial strain or component thereof is for use in combination with an anti-cancer agent.

According to some embodiments, the bacterial strain or component thereof is for use in combination with another type of pathogenic bacterial strain in treating a cancer of the genitourinary system.

The bacterial strain can be administered per se or as a composition comprising the bacteria. According to some embodiments, the bacterial strain is for weekly administration. According to certain embodiments, the bacterial strain is for weekly administration at a unit dosage form comprising from $10^7$ to $10^{12}$ bacterial cells. According to certain embodiments, the bacterial strain is for weekly administration at a unit dosage form comprising from $10^7$ to $10^{12}$ for a period of at least 2 weeks.

The present invention further provides a mutant hemolysin deficient bacterial strain derived from uropathogenic *Escherichia coli* (UPEC), being a mutant of *Escherichia coli* CFT073, wherein the mutant has an insertion in the hemolysin toxin gene, and wherein the mutant is selected from the group consisting of: C93 having an insertion in the hlyA gene, E49 having an insertion in hlyC and D57 having an insertion in hylD. According to some embodiments, the mutant bacterial strain is C93 having an insertion in the hlyA gene.

According to additional aspect, the present invention provides a pharmaceutical composition comprising the bacterial strain and a pharmaceutical acceptable carrier.

According to some embodiments, the pharmaceutical composition is formulated for intravesicular administration.

The present invention further provides a method of treating a cancer of the genitourinary system, the method comprising administering to a subject in need thereof a mutant hemolysin deficient bacterial strain derived from a pathogenic strain of *E. coli* bacterial strain or component thereof.

The present invention further provides a method of treating a cancer of the genitourinary system, the method comprising administering to a subject in need thereof an inactivated *Escherichia coli* uropathogenic strain or component thereof. According to some embodiments the inactivated strain is CFT073. According to particular embodiments the inactivation is by formaldehyde.

The present invention further provides a method of treating bladder cancer, the method comprising intravesicularly administering to a subject in need thereof an inactivated pathogenic *E. coli*. According to some embodiments, the administered inactivated *E. coli* has type I fimbria.

Other objects, features and advantages of the present invention will become clear from the following description, examples and drawings.

BRIEF DESCRIPTION OF THE FIGURES

FIG. 1A is a comparison between C93 cells treatment and *Mycobacterium bovis Bacillus* Calmette-Guerin (BCG) cells treatment, with or without anti-NK antibodies NK1.1. The mice survival percent during the experiment is as indicated. PBS was used as a control.

FIGS. 1B-1D show the effect of hemolysin deficient UPEC C93 on tumor size. Bladder carcinoma was induced in C57BL mice using MB49 bladder carcinoma tumor cells stably transfected with the luciferase (luc) gene (MB49-luc). Mice were treated with BCG, UPEC hemolysin-inactivated C93 mutant or with PBS (negative control) on days 3, 10, 17 and 24 post tumor inoculation. Tumor volume and spread were determined on days 14 (FIG. 1B), 21 (FIG. 1C), and 27 (FIG. 1D) in anesthetized animals by real-time imaging of luciferase expression. Arrows indicate visible tumors.

DETAILED DESCRIPTION OF THE INVENTION

Figure 1A:
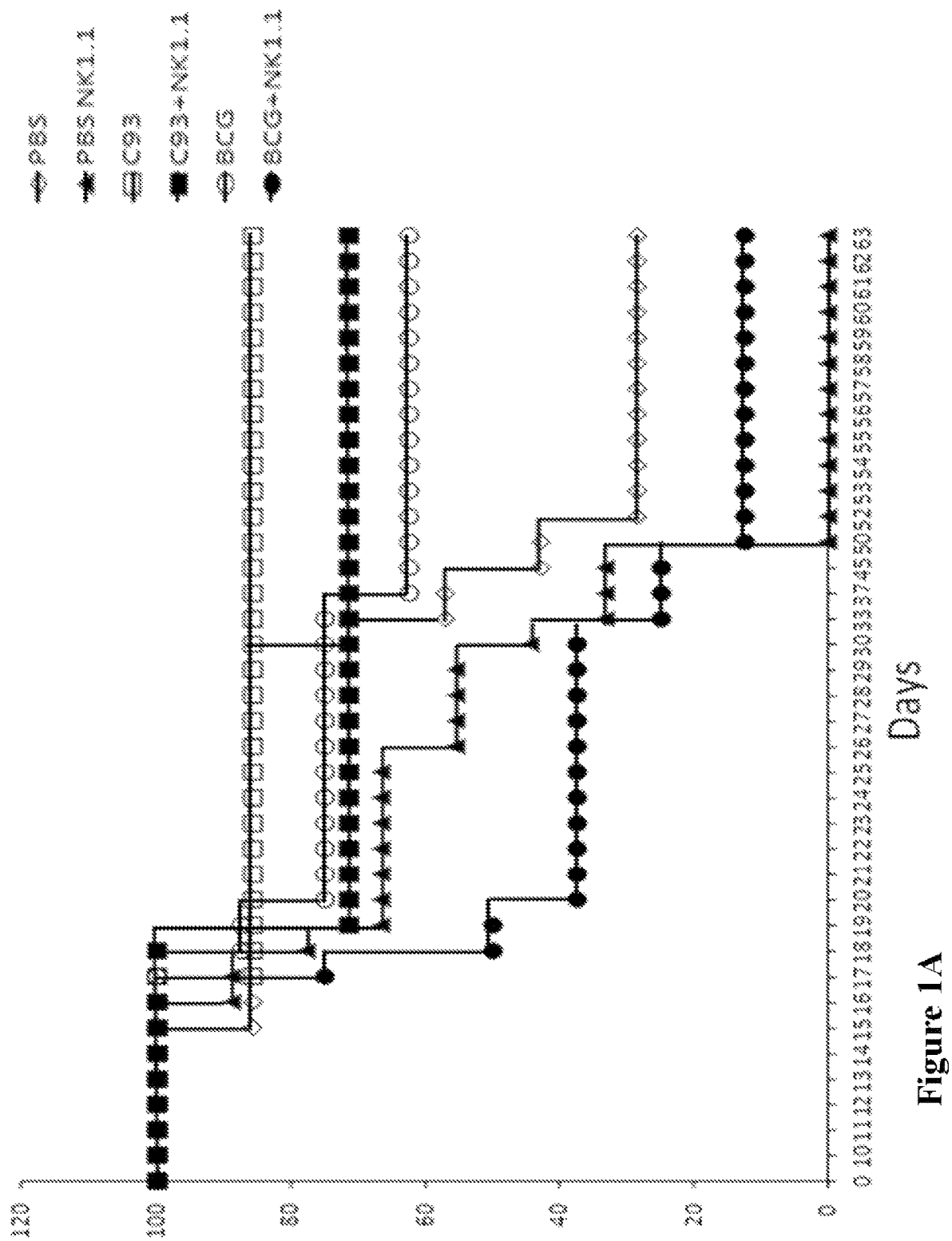
FIGS. 1A-1D show the effect of hemolysin deficient UPEC C93 on the survival of mouse models of bladder cancer.

The present invention provides inactivated pathogenic bacterial strains and use thereof for treating urogenital cancers. The present invention further discloses methods of treating cancers of the genitourinary system using a mutated hemolysin deficient bacterial strain. In addition, methods of treating cancer that comprise the step of directly administering of a mutated or inactivated pathogenic bacterial strain to the cancer site strain are provided.

The methods of the present invention are advantageous over previously known methods for using bacteria in that their ability to depress cells of the immune system is reduced or neutralized. The bacteria of the invention serve as potent and effective agents that recruit the immune system against cancerous cells. The bacteria of the invention may serve as a universal therapy for bladder cancer patients. The therapy does not depend on the adaptive immune system, requiring an early exposure to the bacteria. Without wishing to be bound by any theory regarding the mechanism of action, the bacteria of the invention act locally and recruit immune cells and/or immune related proteins into the cancer site. Moreover, the bacteria of the invention, when intravesicularly administered to mice, do not necessarily activate a systemic immune response, hence having minimal side effects. In addition, the bacteria of the invention proved to be efficient when the bacteria are inactivated. Overall, the bacterial strains disclosed herein seem very promising as an efficacious medication for treating a variety of cancers without causing undesired side effects.

The inventors of the present application have shown that urinary pathogenic *Escherichia coli* adhere to human and murine natural killer (NK) cells primarily through their type I fimbriae and kill NK cells via their hemolysinA toxin. Three strains of urinary pathogenic *E. coli*, mutated in the hemolysinA operon and termed 'C93' (mutated in hlyA), 'E49' (mutated in hlyC), and 'D57' (mutated in hlyD) were prepared. The C93 mutated *E. coli* strain was found to improve the survival of mouse models of bladder cancer. The hlyA gene encodes for the hemolysinA toxin structural protein. In some embodiments hlyA accession number is AE014075.1. The hlyC encodes for the hemolysin-activating lysine-acyltransferase and in some embodiments hlyC Gene ID: 1789689. The hlyD encodes for hemolysin translocator protein. According to some embodiments, the hemolysin is hemolysinA toxin.

The term "hemolysin deficient" refers to a bacterium that completely lacks hemolysin or has a reduced amount of hemolysin by at least 30%, 40%, 50%, 60%, 70%, 80% or 90% compared to the wild type bacterial strain. The term "hemolysin deficient" further refers to a mutated or functionally inactive form of the hemolysin, wherein the mutated form has a reduced activity by at least 25%, 30%, 40%, 50%, 60%, 70%, 80%, or 90% compared to the wild type form. The wild type form of the bacterial strain has active hemolysin.

The term "pathogenic bacterial strain" refers to any bacterial strain that can cause infection.

The terms "urinary pathogenic" and "uropathogenic" are used herein interchangeably.

The term "bacterial strain component" refers to a component of the bacterial strain that is capable of exhibiting an anti-cancer activity in a similar manner as the bacterial strain. Non limiting examples for the component are protein, membrane, and cell wall fraction. According to some embodiments, the bacterial component is an immune stimulating component.

According to certain embodiments, the component is type I fimbria. Type 1 fimbriae are adhesion organelles expressed by many Gram-negative bacteria. They facilitate adherence to mucosal surfaces, particularly to the bladder surface, and inflammatory cells, and contribute to the pathogenesis of *E. coli* in the urinary tract.

The term "has type I fimbria" refers to a bacterial strain that has an active or functioning type I fimbria.

According to some embodiments, the bacterial strain is a mutant strain that overexpresses type I fimbria. As used herein, the term "overexpress" refers to a bacterium that is genetically modified to produce type I fimbria in an amount that is greater than the amount that is produced in an unmodified bacterium. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or up-regulating the endogenous gene, and the like. The type I fimbria overexpression may be produced as described in Chelsea Lane et al. (Journal Of Bacteriology, 2007, Vol. 189, No. 15. p. 5523-5533).

According to certain embodiment, the component comprises Lipopolysaccharides (LPS). Lipopolysaccharides, also known as lipoglycans and endotoxins, are large molecules consisting of a lipid and a polysaccharide composed of 0-antigen, outer core and inner core joined by a covalent bond The terms "cancer" and "cancerous" refer to or describe the physiological condition in mammals that is typically characterized by unregulated cell growth.

The terms "urogenital cancer" and "cancer of the genitourinary system" are used herein interchangeably and refer to any cancer of the genital or urinary system. Non-limiting examples include bladder cancer, kidney cancer, urethral cancer and prostate cancer.

As used herein, the term "subject" refers to any animal, such as a mammal like a dog, cat, livestock, and preferably a human.

The term "treating" a subject for a disease, as used herein, is intended to encompass curing, as well as ameliorating at least one symptom of the disease.

The term "intravesicular" or "intravescial distillation" are used herein interchangeably and refer to a therapy method, in which the drug is inserted directly to the bladder, preferably by catheter.

The term "mutant" as used herein refers to the bacteria of the invention that have been mutated one or more times in, for example, one or more of the hly genes or any other genes that participate in the hemolysin synthesis or expression pathway.

According to some embodiments, the bacterial strain is attenuated or inactivated.

According to some embodiments, the present invention provides attenuated pathogenic bacteria. The term "attenuated," as used herein, describes the diminution in the ability of the bacteria to cause disease in an animal as a whole, e.g., as measured by the LD.sub.50 of the bacteria. More specifically, the pathogenic characteristics of the attenuated bacteria strain have been lessened compared with wild-type bacteria, although the attenuated bacteria are capable of growth and maintenance in culture. An attenuated strain of bacteria according to the present invention is thus one which does not kill an animal to which it is administered, or is one which kills the animal only when the number of bacteria administered is vastly greater than the number of wild type non-attenuated bacteria which would be required to kill the same animal.

According to other embodiments, the bacteria of the invention are inactivated. The term inactivated bacterial strain designates "not live" or "killed" bacteria.

According to some embodiments, the bacterial strain is inactivated by exposure to a fixative compound. According to some embodiments, the bacterial strain is inactivated by a compound selected from the group consisting of: formaldehyde, paraformaldehye, glutaraldehyde, and derivatives thereof. Each possibility represents a separate embodiment of the invention.

Without being bound by any theory or mechanism, it is speculated that formaldehyde inactivation is superior to other inactivation methods in preserving type I fimbria function. It is speculated that the type I fimbria enable the bacterial strain to attach to the bladder wall and not be washed out.

The hemolysin deficient bacteria may be generated by any method as known in the art. A diverse variety of different mechanisms for generating such bacteria are described herein. According to some embodiments, genes that are involved in hemolysin synthesis are mutated. According to exemplary embodiments, the genes are mutated so as to reduce or eliminate their expression. According to additional embodiments, the hemolysin function is altered by providing inhibitors.

According to some embodiments, the hemolysin deficient bacterial strain is a mutated bacterial strain. The term "mutant" as used herein refers to an amino acid, DNA or RNA sequence that is differs from wild type sequence. The mutants of the invention include insertion, deletion and/or substitution of nucleotides in the DNA of the bacterial strain, with the proviso that the mutant/s affects the expression and/or activity of hemolysin. The term "mutant" also refers to any modification of DNA or protein that affects the expression and/or activity of hemolysin.

The term "insertion mutation" refers to the addition of one or more nucleotide base pairs into a DNA sequence.

According to some embodiments, the bacterial strain has a deletion mutation. It is preferred that mutations in the above described genes be introduced as deletions since this will preclude reversion mutations and enhance the safety of the strains containing them. It is preferred to use a scar-less mutation, which refers to a mutation that leaves minimum exogenous sequence ("scar"). In particular, it is important to delete the resistance marker used for the deletion.

According to some embodiments, the hemolysin deficient bacterial strain is a stable hemolysin-A deleted (ΔhlyA) UPEC mutant.

According to certain embodiments, the hemolysin deficient bacteria have only a single type of hly mutation, as described above. In yet other embodiments, the bacteria have two or more of the specific hly mutations.

The hemolysin deficient bacterial strain may have attenuating mutations that improve their safety and suitability for human treatment. The aro genes are required in the biosynthesis of aromatic amino acids and the metabolic intermediate chorismate. Mutations in aro genes are attenuating because the mutants cannot synthesize chorismate, which is required in turn to synthesize folate (not produced by mammals), the major methyl donor in many biosynthetic reactions. Chorismate is also required for the synthesis of enterobactin, a protein involved in the in vivo acquisition of iron. OmpF and OmpC are outer membrane porins that mediate osmoregulation in *E. coli*. Live Enterotoxigenic *Escherichia coli* (ETEC) attenuated by deletions of the genes coding for aroC, ompC and ompF, and the genes for the enterotoxins heat-labile enterotoxin (LT), heat-stable enterotoxin (ST) and Heat-stable enterotoxin 1 (EAST), is used as a commercially available oral vaccine known as ACAM2017 (Acambis plc, Cambridge, UK) that was recently shown to be safe for use even in HIV infected humans. Therefore, it would be useful to attenuate the bacteria by mutating the above described genes. According to some embodiments, the hemolysin deficient bacterial strain is further mutated in at least one gene selected from the group consisting of aroC, ompC and ompF genes. Each possibility represents a separate embodiment of the invention.

According to additional aspect, the present invention provides a mutated hemolysin deficient bacterial strain involved in bladder infection or component thereof for use in treating a cancer of the urinary system.

According to additional aspect, the present invention provides a hemolysin deficient *E. coli* strain or component thereof for use in treating a cancer of the urinary system or prostate cancer. According to some embodiments, the hemolysin deficient *E. coli* strain or component thereof is for use in treating bladder cancer.

According to additional aspect, the present invention provides an inactivated uropathogenic *E. coli* (UPEC) for use in treating a cancer of the urogenital system.

According to additional aspect, the present invention provides an inactivated enteropathogenic *E. coli* for use in treating a cancer of the urogenital system.

According to another aspect, the present invention provides a method of treating a cancer of the urogenital system in a subject in need thereof, comprising directly administering to the bladder of said subject a mutant hemolysin deficient bacterial strain or component thereof. According to some embodiments, the bacterial strain is *E. coli*. According to certain embodiments, the bacterial strain is UPEC. According to other embodiments, the bacterial strain is EPEC.

According to some embodiments, the bacterial strain exhibits at least one biological activity selected from the group consisting of: stimulating the antitumor cytolytic activity of lymphocytes and/or NK cells; recruiting T-cells and neutrophils; stimulating proliferation of NK cells; and inducing regression of established tumors and/or of primary solid tumors. Each possibility represents a separate embodiment of the invention.

According to additional aspect, the present invention provides a method of treating a bladder cancer, the method comprising directly administering to the bladder of a subject in need thereof an inactivated *Escherichia coli* strain CFT073 or component thereof. According to some embodiments, the method comprises a local administration at or in proximity to the cancer site.

According to additional aspect, the present invention provides a method of treating a cancer of the urogenital system in a subject in need thereof, comprising administerin a *E. coli* bacterial strain, said bacterial strain overexpresses type I fimbria.

According to Additional aspect, the present invention provides a pathogenic *E. coli* bacterial strain for use in treating a cancer of the genitourinary system, wherein the bacterial strain overexpresses type I fimbria.

According to Additional aspect, the present invention provides a pathogenic *E. coli* bacterial strain for use in treating a bladder cancer, wherein the bacterial strain overexpresses type I fimbria.

According to some embodiments, the bacterial strain is inactivated. According to certain embodiments, the bacterial strain is inactivated by formaldehyde.

Administration

The bacteria of the invention can be administered using any known practice. In some embodiments, the bacterial strain is administered to the patient parenterally. According to some embodiments, parenteral administration is administration intravesicularly, intravenously, intramuscularly, intraperitoneally, intradermally, buccally, transdermally, intradermally, intraviterally or subcutaneously. Each possibility represents a separate embodiment of the invention.

According to exemplary embodiments, the bacterial strain of the invention is intravesicularly administered. In certain embodiments, the bacterial strain is administered directly, or adjacent to the site of the cancer.

Pharmaceutical Compositions

The present invention provides in some embodiments pharmaceutical compositions comprising the bacterial strain or component thereof and a pharmaceutically acceptable carrier, excipient or diluent.

The term "pharmaceutical composition" as used herein refers to any composition comprising at least one pharmaceutically active ingredient, formulated such that it facilitates accessibility of the active ingredient to the target organ.

The compositions of the invention may include the whole bacteria, or may include extracts and/or components such as cell wall or cell membrane extracts that exhibits the anticancer activity according to the invention.

The compositions of the invention may be administered alone or in combination with other compounds, and in the present of an adjuvant, buffer or carrier. The buffer or carrier include, but not limited to, water for injection or physiological saline.

According to some embodiments, the bacterial strain or component thereof is for use in combination with an anticancer agent.

According to some embodiments, the composition is formulated for intravesicular administration. According to certain embodiments, the bacterial strain or composition comprising the bacterial strain is provided in a dosage form. According to some embodiments, the dosage form is administered in an amount selected from 1 ng/kg to 1 g/kg, 10 ng/kg to 0.1 g/kg, 50 ng/kg to 10 mg/kg, 0.1 µg/kg to 1 mg/kg, and 0.2 µg/kg to 0.2 mg/kg body. Each possibility represents a separate embodiment of the invention. It may be appropriate to administer the required dose as two, three, four or more sub-doses at appropriate intervals throughout the day.

According to some embodiments, the treatment period is at least 1 week, at least 2 weeks, at least 4 weeks, at least 1 month, at least 2 months, at least 3 months, at least 4 months, least 6 months, or at least 1 year. In some embodiments the treatment period is from 1 day to 1 week, from 1 week to 4 weeks, from 1 month to 3 months, from 3 months to 6 months, from 6 months to 1 year, or for over a year. Each possibility represents a separate embodiment of the invention.

According to some embodiments, from $10^6$ to $10^{12}$ microorganisms total may be administered to the patient in a given dosage form. According to certain embodiments, from $10^7$ to $10^{10}$ microorganisms total may be administered to the patient in a given dosage form. According to additional embodiments, an effective amount may be provided in an amount of from 0.5 ml to 40 ml of the bacterial composition having from $10^6$ to $10^{11}$ bacteria per ml.

Any of the preparations described herein may be administered as a single treatment or as multiple treatments, such as once a week for several weeks, or the composition may be administered intermittently according to a set schedule, e.g., once weekly, once monthly, or when the patient relapses from the primary illness.

EXAMPLES

Example 1—Effect of Hemolysin Deficient UPEC C93 on the Survival of Mouse Models of Bladder Cancer Hemolysin Deficient Mutants:
Construction of UPEC CFT073 (deposited under ATCC®700928™) Transposon Library: EZ::TnKan transposomes (Gur et al., Cell Host Microbe. 2013 Dec. 11; 14(6):664-74) were purified from the pMODKan plasmid according to manufacturer's instructions and electroporated into UPEC CFT073 bacteria harboring a GFP-expressing pCM18 plasmid. The library was screened to identify the genes involved in NK cells killing by incubating the mutants for 3 hours with NK cells at 37° C. More than 1000 mutated clones were screened. Three mutants were identified, having an intact adhesion ability, but impaired killing activity. To determine the transposon location genomic DNA was purified from the selected clones (GenElute, Sigma) and restricted with HpaI, MfeI, and NdeI (New England Biolabs) which do not cleave within the inserted transposon. The resulting fragments were then self-ligated (TaKaRa) and used as a template for inverse PCR (Herculase II, Agilent) for amplification of the transposons' flanking sequences. The generated sequences were blasted against the CFT073 genome to determine the location of the insertion mutation. The disrupted genes of the three mutants were identified and were found to reside in the hlyA operon that encodes for the hemolysinA toxin: 'C93' (mutated in hlyA), 'E49' (mutated in hlyC), and 'D57' (mutated in hlyD) (Gur et al., Cell Host Microbe. 2013 Dec. 11; 14(6):664-74).

Transitional Cell Cancer (TCC):
MB49 bladder cancer cells line, derived from C57/B16 mice were injected/implanted intravesically into female mice using a protocol described by Günther et al. (Cancer Research, 2834-2837, 59 Jun. 1, 1999). Briefly, female mice (10-12 mice per group), 8-10 weeks age were anesthetized with Ketamine/Xalazine. An area of about 1 cm$^2$ on the back of the animal was shaved and then the mice were placed on a ground plate of the cautery unit. The urinary bladder was catheterized with Teflon catheter 25-gauge and a soft tipped guide wire 24-gauge (0.7×19 mm) was inserted until it touched the bladder wall. The guide wire was attached to the cautery unit and monopolar coagulation current was applied for 5 seconds at the lowest power setting. After removal of the wire, 50 µl of DMEM MB49 tumor cell suspension (30000 tumor cells per mouse) were instilled. Then, the catheter was clamped and left in the bladder for 2-3 hours while the mouse is anaesthetized. MB49-luc stably transfected with luciferase were used, enabling the monitoring of the tumors with CCCD camera.

Intravesical Treatment:
Two days following tumor cells implementation, the mice were randomized into 6 groups and received various treatments through intravesicl instillation once a week. The bacteria or PBS were injected through catheters inserted into the bladders.

Group 1: Treatment with PBS. The first intravesicl instillation was 3 days following TCC inoculation, than every week (5 injections total).

Group 2: Treatment with PBS as described for group 1 and anti-NK1.1 (mAb PK136, by intraperitoneal injection) twice a week (on day 1, on day 4 and then every week for 6 weeks).

Group 3: Treatment with 50 µl containing $10^9$/ml C93 bacteria. The first intravesicl instillation was 3 days following TCC inoculation, than every week (5 injections total).

Group 4: Treatment with 50 µl containing $10^9$/ml C93 bacteria as described for group 3 and anti-NK1.1 (mAb PK136) twice a week (on day 1, on day 4 and then every week for 6 weeks).

Group 5: Treatment with an Onco-Tice® BCG strain (2-8×$10^8$ CFU per vial). The vial was reconstituted in 3 ml of normal saline and 0.05 ml were injected per mouse. The first intravesicl instillation was 3 days following TCC inoculation, than every week (5 injections total).

Group 6: Treatment with an Onco-Tice® BCG strain as described above in combination with anti-NK1.1 (mAb PK136) twice a week (on day 1, on day 4 and then every week for 6 weeks).

The mice were examined daily on the first week and then 3 times a week. The tumor progression was monitored weekly using CCCD imaging. For Luciferase assay/CCCD imaging in vivo the mice were anesthetized with Isofluran. The luciferin was injected IP in an amount of 125 µg/g body weight and the imaging was performed in 5-10 minutes.

All mice were sacrificed on day 62 after tumor implementation using ketamin/xylasin anesthesia with subsequent neck dislocation.

Experimental Procedure:
Day −1: Examining MB49 tumor cell line for luciferase and NK1.1 injection (100 microgram per mouse) for mice of groups 2, 4, and 6.
Day 0: tumor implementation.
Day 3: Treatment with PBS, C93, or BCG as described above and NK1.1 injection (100 microgram per mouse) for mice of groups 2, 4, and 6.
For the remaining 5.5 weeks after tumor implantation:
Treatment with PBS, C93, or BCG once a week.
CCCD imaging once a week
Results:
To examine the effect of hemolysin deficient bacteria on cancer, bladder cancer was induced in mice, and the survival rate and tumor size of mice treated with C93 cells were measured. C57BL mice (10 mice per group), were inoculated in the bladder with MB49 bladder carcinoma cells. As described above the mice were treated with PBS, C93, or BCG, with or without NK1.1 mAb, antibodies that deplete NK cells.

Figure 1B:
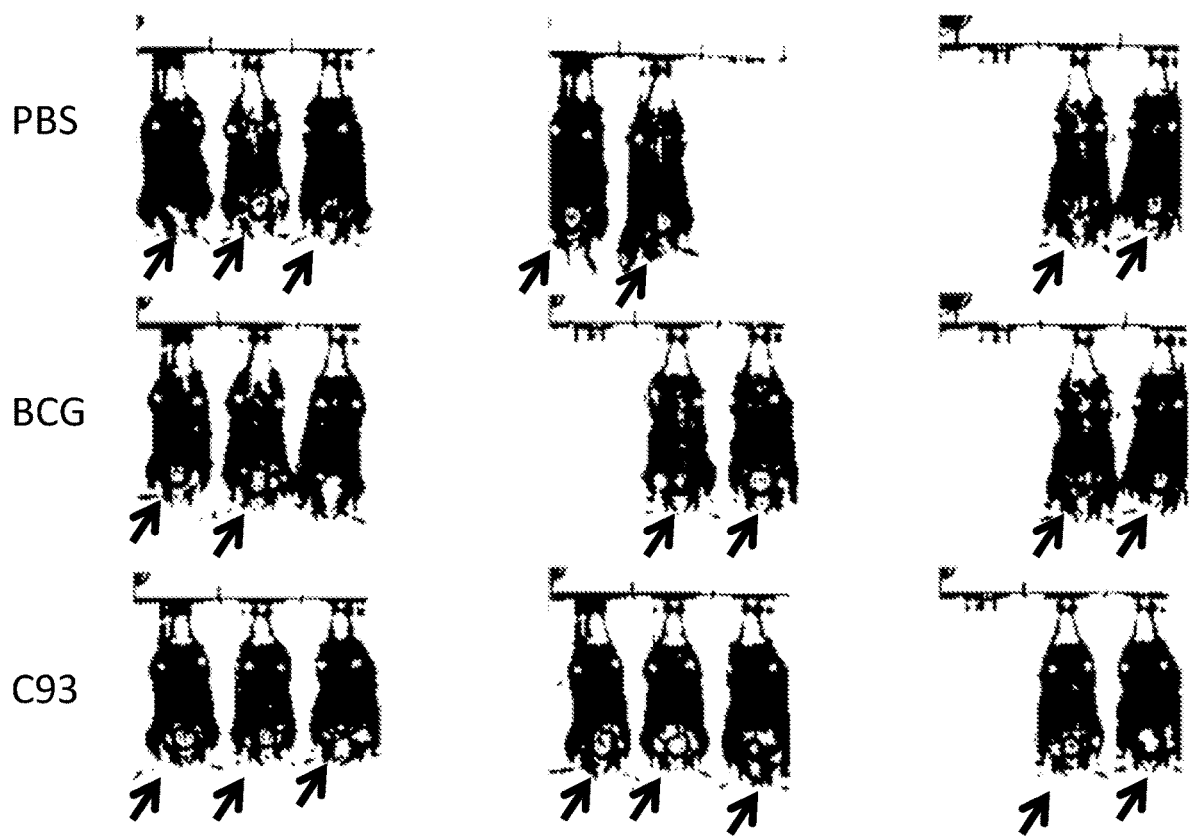
Figure 1C:
Figure 1D:
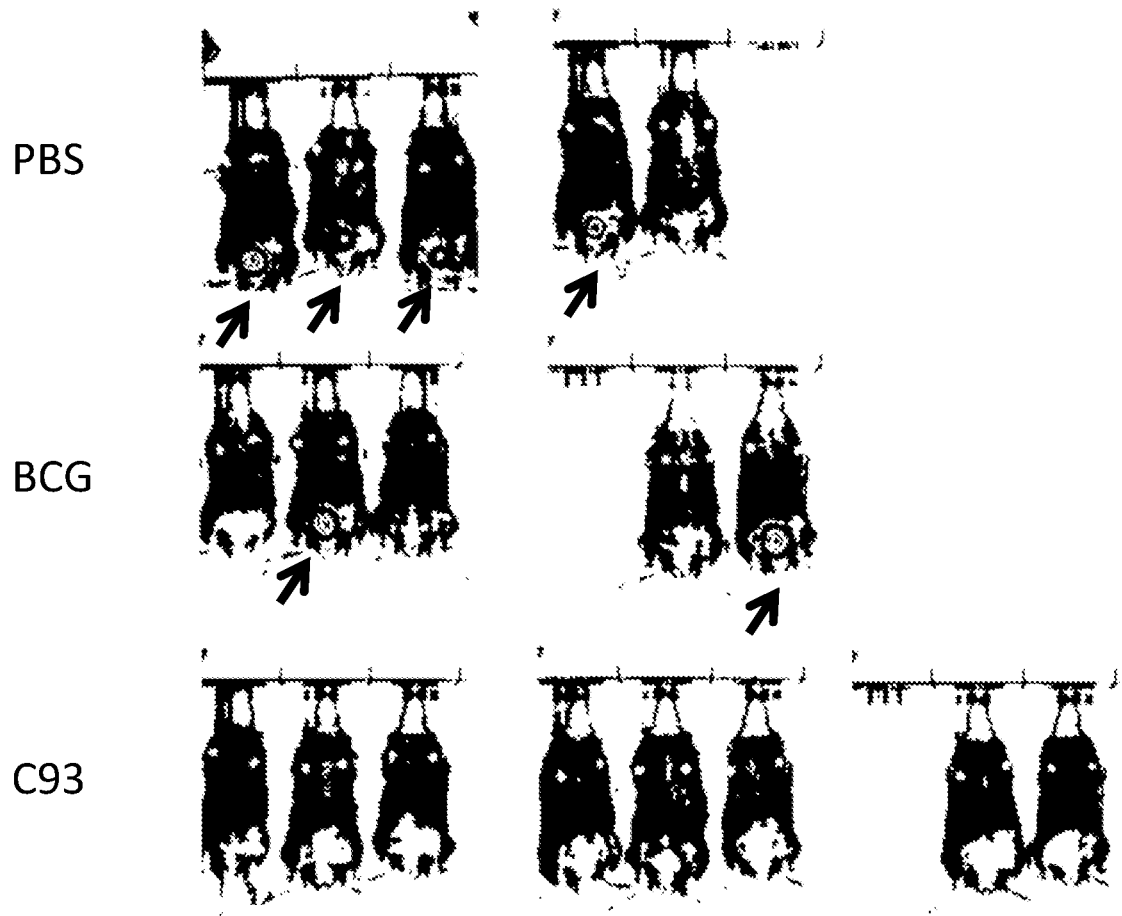
Figure 3A:
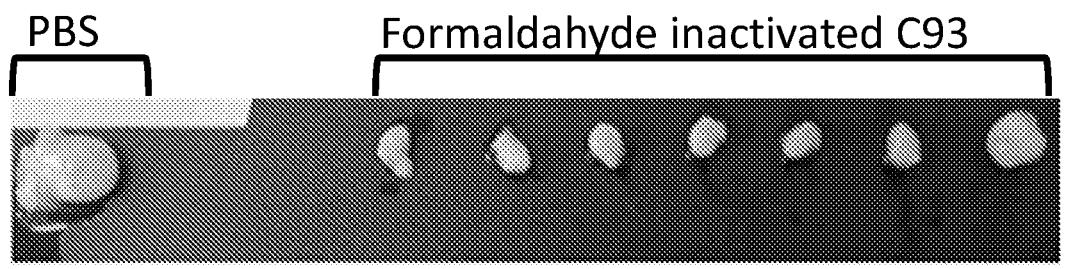
FIGS. 3A-3B show the effect of formaldehyde inactivated C93 or UPEC treatments on bladder morphology in mouse models of bladder carcinoma. Bladder carcinoma was induced in C57BL mice using MB49 bladder carcinoma tumor cells. The mice treated with PBS (negative control), with formaldehyde-inactivated C93 UPEC mutant (FIG. 3A), or with formaldehyde-inactivated wild type UPEC (CFT073)(FIG. 3B). At day 56 post tumor inoculation, bladders were collected from the surviving mice and photographed.

As shown in FIG. 1A, treatment of bladder cancer with C93 increases survival rate when compared with BCG treatment or control. Surprisingly, C93 treatment was almost unaffected by NK cells depletion, having compelling anticancer activity. In contrast, BCG treatment was highly affected by NK cells depletion. Remarkably, all of the C93 treated mice survived the study. In addition, C93 treatment induced tumor regression. Most mice had large and visible tumors on day 14 after tumor cells implantation. Remarkably, no visible tumors were observed in mice treated with C93 cells after 27 days. In contrast, mice treated with PBS and several of the BCG treated mice had visible tumors (FIGS. 1B-1D). At day 56 post tumor inoculation, bladders were collected from the surviving mice and photographed. FIG. 3A demonstrates that the bladders of mice treated with C93 appear normal. In contrast, the bladder of a mouse treated with PBS is enlarged and misshaped.

Example 2—Effect of Inactivated UPEC on the Survival of Mouse Model of Bladder Cancer UPEC CFT073 were exposed to formaldehyde (4% in PBS) overnight, washed three times and brought to OD=1 (approximately $10^9$ cells/me.

To test whether all bacteria were killed by the formaldehyde treatment, 100 µl of the OD=1 suspension were plated in 1:1, 1:10, and 1:100 dilutions and incubated overnight at 37° C. No growth was detected, confirming bacterial inactivation.

The amount of residual formaldehyde in the bacterial preparation was measured using the Formaldehyde VACUettes Kit (Catalog No. K-4605D) chemetrics (VA. USA) and found to be 0-5 ppm (0.0005%) (n=3).

Figure 2:
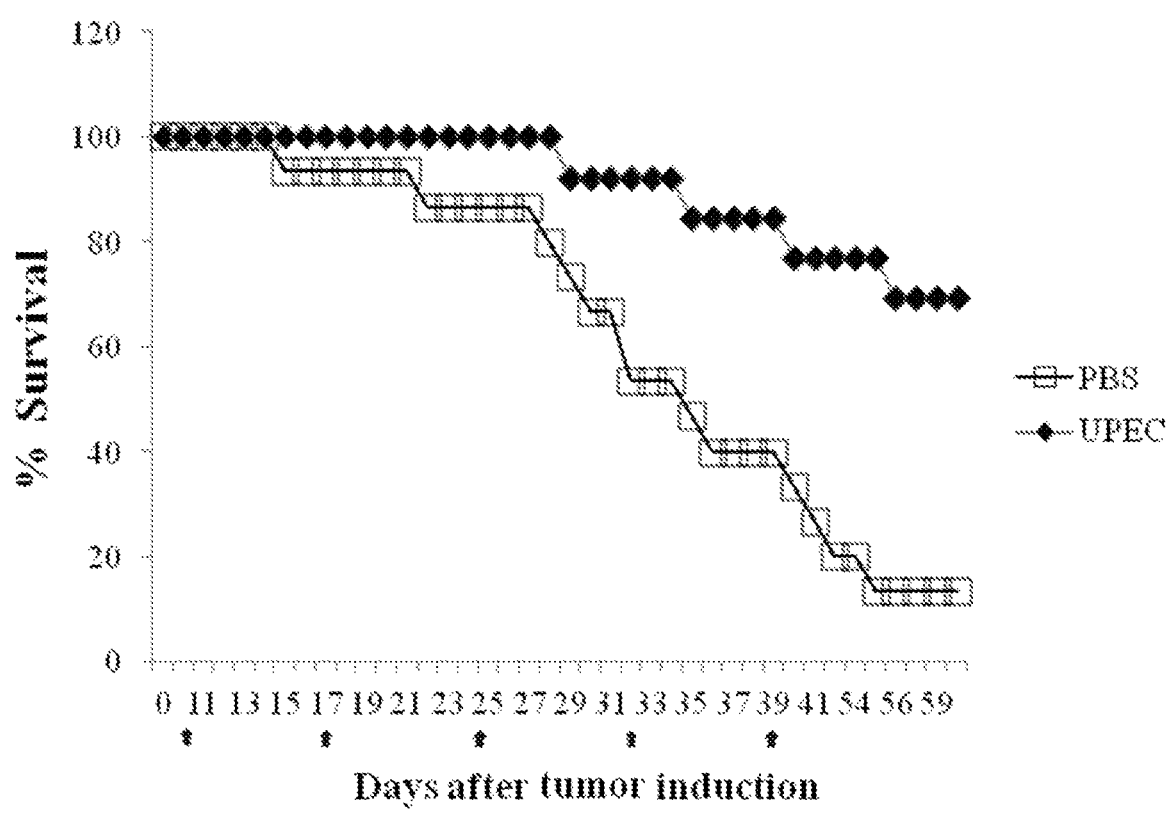
FIG. 2 shows the effect of formaldehyde-inactivated wild type UPEC (CFT073) on the survival of mouse models of bladder carcinoma. Bladder carcinoma was induced in C57BL mice using MB49 bladder carcinoma tumor cells. Ten days later the mice were treated with $10^8$ cells of wild type UPEC CFT073 inactivated with formaldehyde. Weekly treatments were continued for 30 days (arrows indicate day of treatment). PBS was used as a negative control.
Figure 3B:
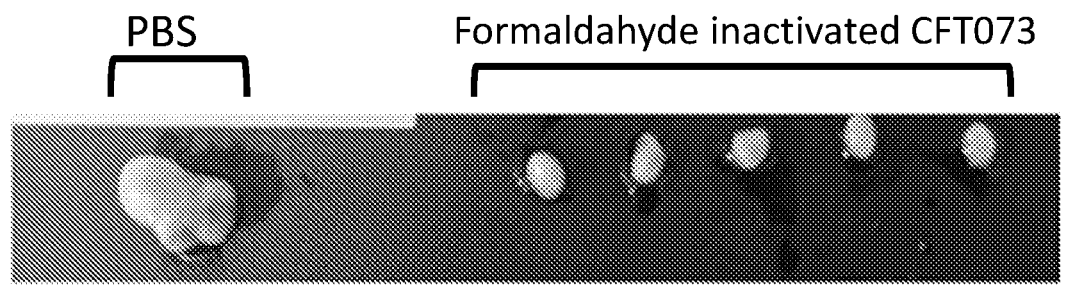

Next, the effect of formaldehyde inactivated bacteria on the survival rate of mouse models of bladder cancer was examined MB49 bladder carcinoma cells were inoculated into the bladder of C57BL mice. Treatments started ten days after cancer inoculation. Mice were treated weekly (days marked with arrows; FIG. 2) with PBS (negative control), or with $10^8$ cells of wild type UPEC strain CFT073 which were inactivated with formaldehyde. FIG. 2 shows that treatment with formaldehyde inactivated UPEC is highly effective against bladder carcinoma. The survival rate of mice treated with inactivated UPEC strain CFT073 was dramatically increased. At day 56 post tumor inoculation, bladders were collected from the surviving mice and photographed. FIG. 3B demonstrates that the bladders of mice treated with CFT073 appear normal. In contrast, the bladder of a mouse treated with PBS is enlarged and misshaped.

Example 3—Effect of Inactivated Enteropathogenic E. coli (EPEC) on the Survival of Mouse Model of Bladder Cancer To further and examine the effect of inactivation by formaldehyde, the survival rate of mouse models of bladder cancer treated with UPEC or EPEC which were inactivated by formaldehyde was examined MB49 bladder carcinoma cells were inoculated into the bladder of C57BL mice. The mice were treated weekly with $3 \times 10^8$ cells/mouse UPEC (CFT073 FA), EPEC (EPEC FA), and *Helicobacter pylori*, starting day 10 after TCC inoculation.

Figure 4:
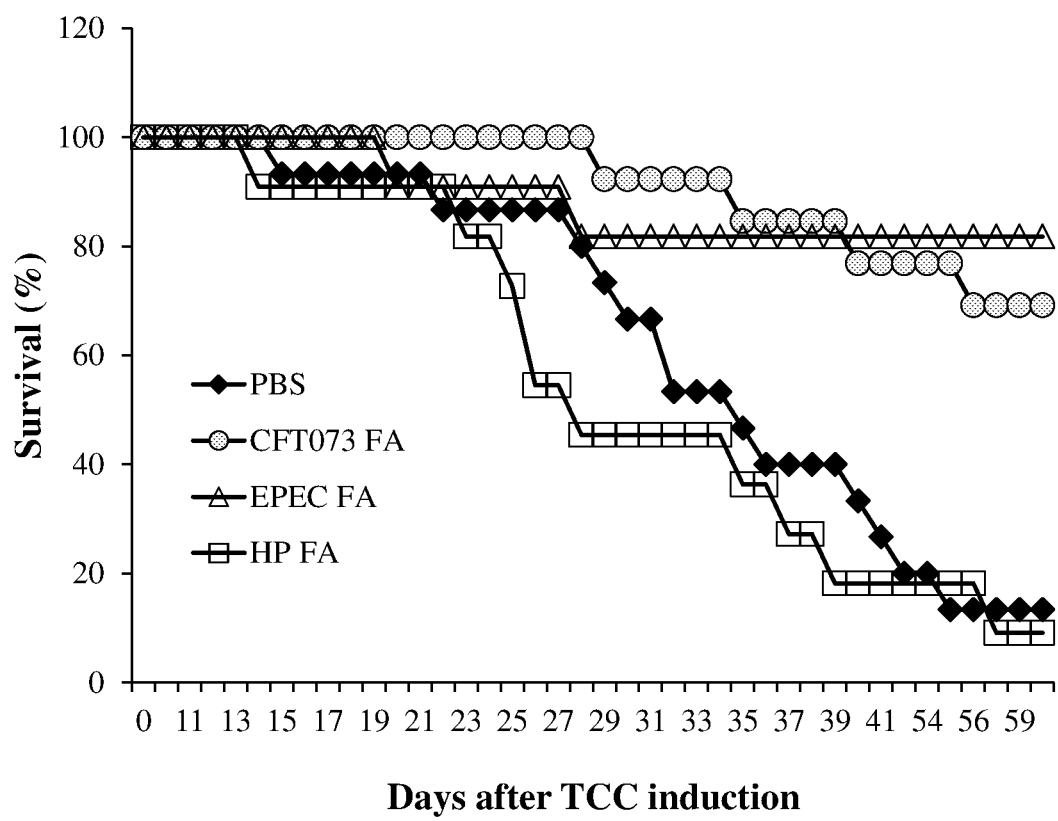
FIG. 4 shows the effect of formaldehyde inactivated UPEC (CFT073 FA), Enteropathogenic *E. coli* (EPEC FA), or *Helicobacter pylori* (HP FA) treatment on the survival of mouse models of bladder carcinoma. PBS was used as a negative control.

As shown in FIG. 4, mice bearing a bladder cancer treated with UPEC and EPEC exhibited significantly higher survival rate as compared to *Helicobacter pylori* treatment and control (PBS).

Figure 5:
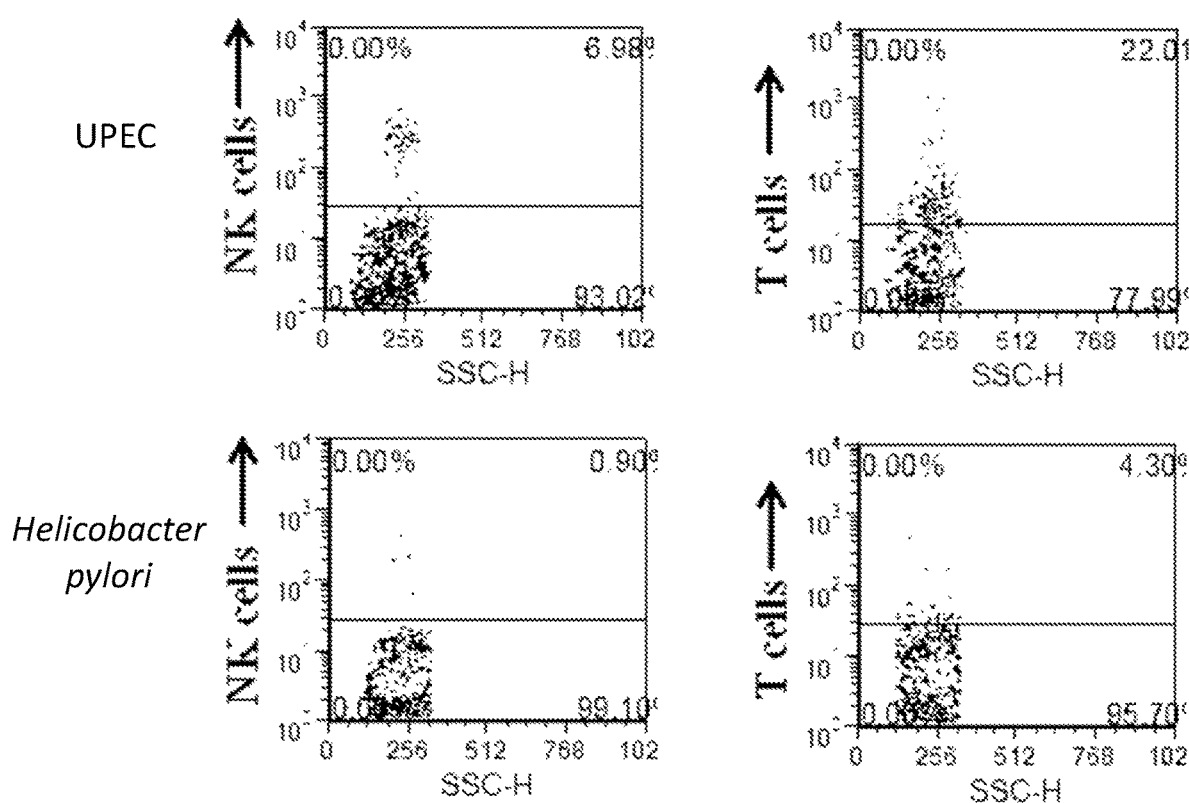
FIG. 5 shows the effect of formaldehyde inactivated UPEC and *Helicobacter pylori* on local recruiting of immune cells. $10^8$ of formaldehyde-inactivated UPEC or *Helicobacter pylori* were inoculated into the bladder of mice. Mice were sacrificed 2 days later and NK and T cells were quantified by flow cytometry.

Example 4—Inactivated Wild Type UPEC but not Helicobacter pylori Attract T and NK Cells to the Bladder The ability of UPEC bacteria to recruit immune cells was examined. $1 \times 10^8$ of formaldehyde inactivated UPEC CFT073 or *Helicobacter pylori* were inoculated into the bladder of mice. Two days later the mice were sacrificed and NK and T cells were quantified by flow cytometry. As showed in FIG. 5, the number of NK cells and T cells (upper panel; 6.9% and 22%, respectively) in UPEC inoculated mice bladders was significantly higher compared to bladders inoculated with *Helicobacter pylori* (lower panel; 0.9% and 4% for NK and T cells, respectively).

Figure 6:
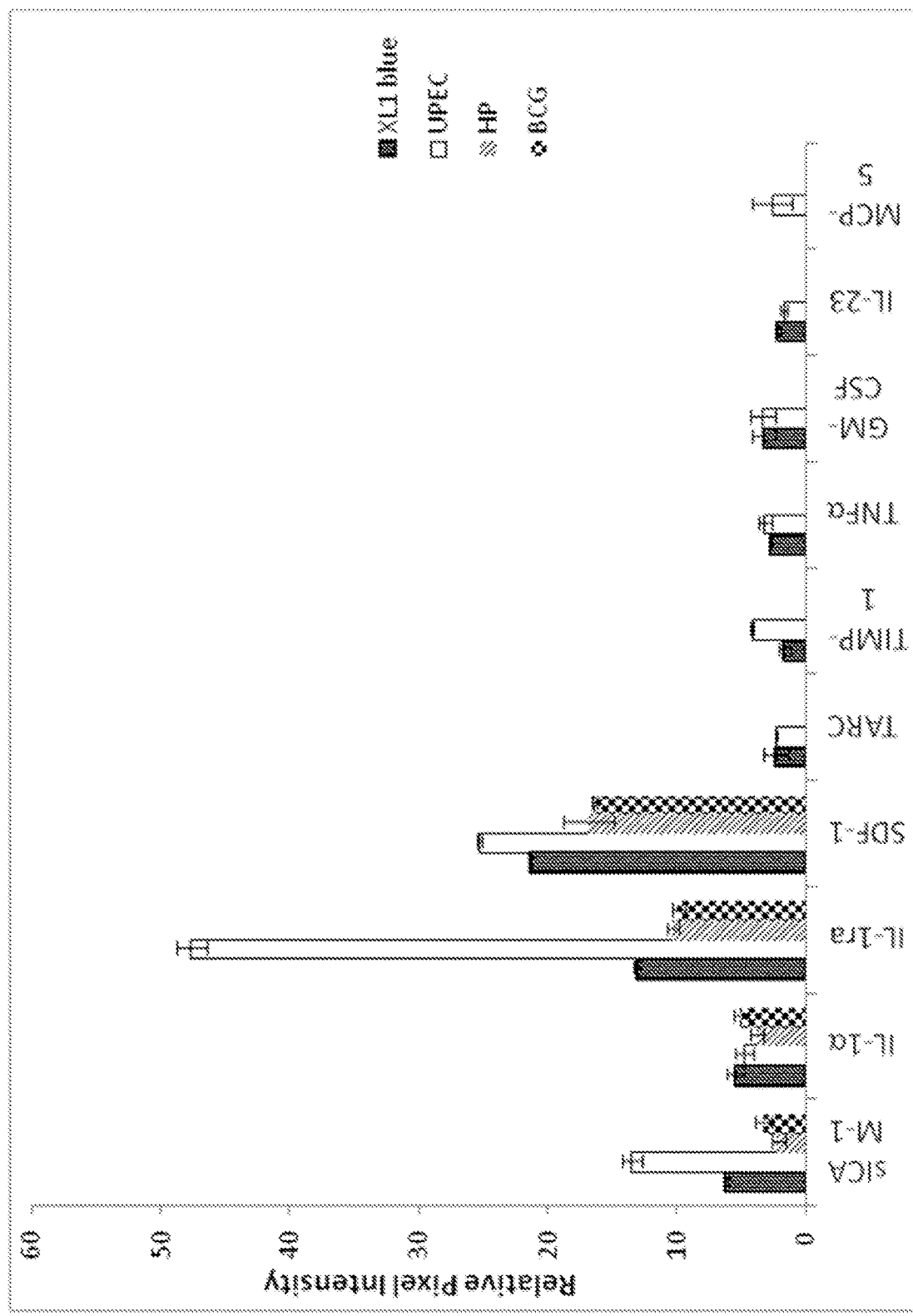
FIG. 6 shows relative cytokine/chemokine amounts in bladders of mouse models of bladder carcinoma that were treated with different strains of bacteria. $1\times10^8$ cells of formaldehyde-inactivated (FA) UPEC CFT073, *E. coli* XL1 blue (laboratory strain of *E. coli*), *Helicobater pylori* or BCG were inoculated into the bladders of each mouse. Standard commercial array was used to quantify relative cytokine/chemokine amounts.

Next, the cytokins/chemokines response profile following bacterial inoculation was examined $1 \times 10^8$ of formaldehyde-inactivated (FA) UPEC CFT073, *E. coli* XL1 blue (laboratory strain of *E. coli*), *Helicobater pylori* or BCG were inoculated into the bladders of each mouse. After 2 days the mice were sacrificed and bladder cytokines/chemokines were quantified using a cytokine array. Remarkably, the amounts of several cytokines and other immune related molecules, such as IL-1ra and sICAM-1, were significantly higher in bladders inoculated with formaldehyde inactivated (FA) UPEC when compared to inoculation with other types of bacteria (FIG. 6).

Overall, these results suggest that inactivated UPEC induce a local immune response.

Example 5—Formaldehyde Inactivated E. coli Strains have a Superior Anticancer Activity Compared to Heat Shock Killed Bacteria Next, a comparison between formaldehyde inactivation and heat shock inactivation was performed. Mice bearing MB49 bladder carcinoma cells were treated weekly with formaldehyde inactivated UPEC strain CFT073 or C93 mutant, and CFT073 or C93 strains that were killed by heat. The procedure was performed as described in example 1. Control mice received PBS.

Figure 7:
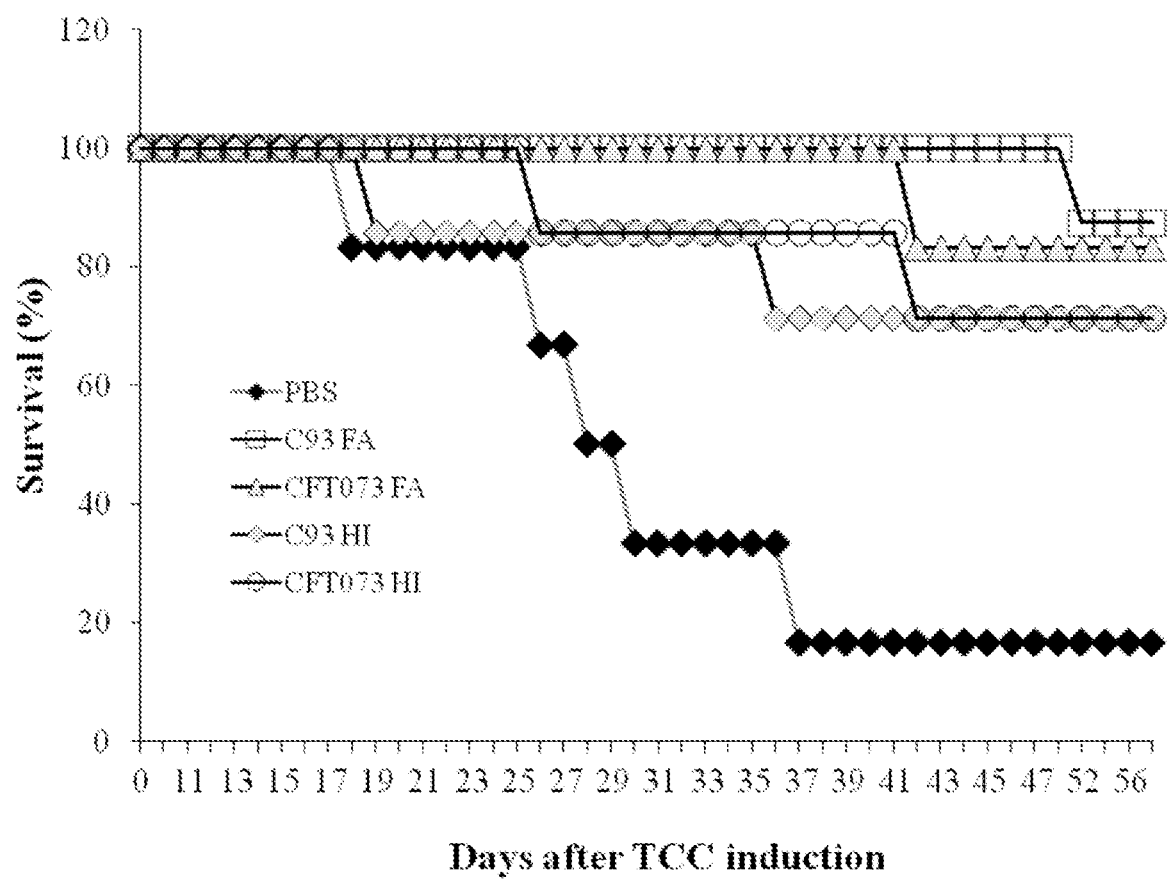
FIG. 7 shows the effect of formaldehyde inactivated UPEC (CFT073 FA), formaldehyde inactivated C93 (C93 FA), heat inactivated UPEC (CFT073 HI), or heat inactivated C93 (C93 HI) treatments on the survival of mouse models of bladder carcinoma. The survival rate percent after transitional cell carcinoma (TCC) induction is as indicated. PBS was used as a negative control.

FIG. 7 demonstrates that treatment with bacteria that were inactivated with formaldehyde is superior to treatment with heat inactivated bacteria, showing an improved survival rate.

Example 6—Effect of Administration Route on Immune Cells Recruitment

To examine the effect of route of administration, mice were inoculated intravesicularly or subcutaneously with $10^8$ formaldehyde inactivated UPEC CFT073 (N=5 per group). After 48 hours bladders were harvested and Peripheral Blood Lymphocytes (PBLs) were extracted from the bladders and analyzed using cell cytometry.

Figure 8:
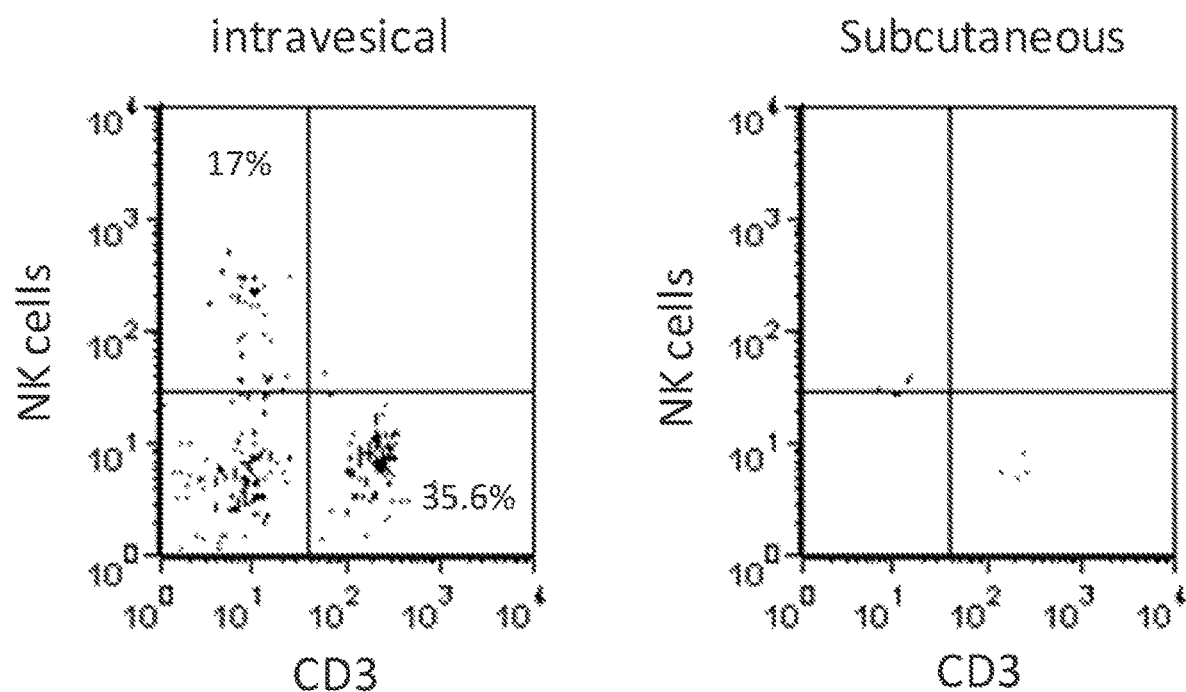
FIG. 8 shows the effect of administration route on immune cells recruitment. Mice were inoculated intravesicularly or subcutaneously with $10^8$ formaldehyde inactivated UPEC CFT073 (N=5 per group). After 48 hours bladders were harvested and Peripheral Blood Lymphocytes (PBLs) were extracted from the bladders and analyzed using cell cytometry.

As shown in FIG. 8, PBLs number was significantly higher (150,000 vs. 1,400 in total counting) in the bladder of mice inoculated intravesicularly, out of which 17% were T cells (CD3 positive) and 17% were GFP-expressing NK cells.

Example 7—Effect of Bacterial Membrane and Bacterial Membrane Protein Extraction on the Survival of Mouse Model of Bladder Cancer Bacterial Membrane and Membrane Protein Extraction:
Bacterial cells are grown overnight and washed in PBS and resuspended in PBS supplemented with 3 mM PMSF (Sigma-Aldrich, Germany) A French press (8,000 psi×3 times) is used to disrupt the cells, and unbroken cells are removed by sedimentation at 10,000×g at 4° C. for 10 minutes.

Alternatively, cells are disrupted using glass beads. Cell suspensions are placed in 2 ml microfuge tubes containing 600 µl of glass beads (106 µm, Sigma). Cells are then disrupted two to four times using the FastPrep cell disruptor (Bio 101, Savant Instruments, Inc., NY, USA) at a speed of 6 m/s for 45 s, with ice-cooling between disruptions. The lysates are centrifuged at 10,000×g for 5 min.

The supernatant is collected and subjected to high-speed centrifugation (150,000×g at 4° C. for 1 hour), and the resulting pellet containing the cell walls is washed twice, resuspended in sodium phosphate buffer and kept at −80° C. until used. To determine proteins amount and integrity, a sample of each pelleted membrane is boiled in SDS-PAGE sample buffer for 10 minutes, and fractioned using SDS-PAGE (12% and 4%) to visualize protein bands.

Outer Membrane Vesicle Preparation:

Stationary cultures are harvested by centrifugation at 10,000×g for 20 min at 4° C. Culture supernatants are collected and filtered through a 0.2 µm filter (Whatman Schleicher & Schuell). Cell-free supernatants are centrifuged at 100,000×g for 2 hr. The supernatant is discarded and the pellet containing the vesicles is washed twice with Tris-buffered saline (TBS, 0.05 M Tris-HCl [pH 7.8], 0.1 M NaCl) by centrifugation at 100,000×g. The pellet is stored at −20° C. until further use.

Bacterial Lysate:

Bacterial cells are grown overnight, washed in PBS and resuspended in PBS supplemented with 3 mM PMSF (Sigma-Aldrich, Germany).

Cell suspensions are placed in 2 ml microfuge tubes containing 600 µl of glass beads (106 µm, Sigma). Cells are disrupted two to four times using the FastPrep cell disruptor (Bio 101, Savant Instruments, Inc., NY, USA) at a speed of 6 m/s for 45 s, with ice-cooling between disruptions. The lysates are centrifuged at 10,000×g for 5 min and the supernatant fluid is collected.

The bacterial lysate bacterial protein extract and membrane fraction are administered to mouse model of bladder cancer as describe in the previous examples. The survival rate and tumor size are examined.

Example 8—Clinical Trial of Bacterial Strains According to any of the Above Embodiments A clinical study is designed for assessing the effect of the bacterial strains on bladder cancer patients. The primary objective is to assess efficacy and safety of the formaldehyde inactivated Uropathogenic *E. coli* CFT073 given as six intravesical instillations of $10^{10}$ inactivated-CFU (or cells) per instillation. The primary efficacy objective is to determine the ability of the treatment to prevent the tumor recurrence after 6 weekly intravesical instillations of the tested product. The recurrence is assessed 8-10 weeks following commencement of the treatment. The primary safety objective is to determine adverse effects induced by the tested product. Secondary objectives include determining the long term (one year) freedom of the cancer recurrence and time to tumor recurrence in patients free of tumor who did not recur after 8-10 weeks.

Study Design:

Subject recruitment—The patients are recruited through the urologic oncology clinic in Hadassah Medical Center, Israel.

Subject inclusion criteria—Patients that underwent complete transurethral excision of recurrent, intermediate to high risk for recurrence non-muscle invasive bladder cancer (NMIBC), and have a history of at least one course of adjuvant immunotherapy or chemotherapy intravesical treatment prior to this recurrence.

Subject Exclusion Criteria:
i. Pregnant or breast feeding women
ii. T1 High grade urothelial carcinoma of bladder
iii. Concomitant upper tract urothelial carcinoma
iv. TCC in bladder diverticulum or prostatic urethra
v. Muscle invasive UC
vi. Metastatic UC
vii. Karnofsky's performance status <60
viii. Known immunodeficiency status
ix. Active urinary tract infection
x. other active malignancy The patients that consented to participate in the study start the treatment within 4-5 weeks after a Transurethral resection of the bladder tumour (TURBT). The patients are treated with weekly intravesical instillation of formaldehyde-inactivated UPEC for 6 weeks. The product is given through 12 French Tiemann urethral catheter and patients are asked to refrain from voiding for 2 hours.

Subject Follow-Up:

Urine culture, urinalysis, cystoscopy and urine cytology tests are performed 2 months following the last intravesical treatment and every 4 months for 2 years thereafter.

TABLE 1

Course of treating, safety and disease assessment.

| | Screening | | Visit # | | | | | | |
|---|---|---|---|---|---|---|---|---|---|
| | | | 1 | 2 | 3 | 4 | 5 | 6 | 7 |
| | | | Study Week (W) | | | | | | |
| | Weeks −4 to −1 | Week −2 (range −4 to −1) | W1 | W2 | W3 | W4 | W5 | W6 | W14-15 |
| | | | | Every 7 days (window 5-9 days) | | | | | |
| Informed consent | X | | | | | | | | |
| Demographics | X | | | | | | | | |
| Physical exam | X | | | | | | | | |
| Vital Signs | X | | X | X | X | X | X | X | X |
| Medical + Bladder cancer history | X | | | | | | | | |
| Urinalysis | X | | | | | X | | | X |
| Hematology[a] | X | | | | | X | | | X |
| Blood chemistry[b] | X | | | | | X | | | X |
| β-hCG (females)[c] | X | X | | | | | | | |

TABLE 1-continued

Course of treating, safety and disease assessment.

| | Screening | | Visit # | | | | | | |
|---|---|---|---|---|---|---|---|---|---|
| | | | 1 | 2 | 3 | 4 | 5 | 6 | 7 |
| | | | Study Week (W) | | | | | | |
| | Weeks −4 to −1 | Week −2 (range −4 to −1) | W1 | W2 | W3 Every 7 days (window 5-9 days) | W4 | W5 | W6 | W14-15 |
| Karnofsky's score | X | | | X | | | | | X |
| Cystoscopy | X | | | | | | | | X |
| Urine cytology | X | | | | | | | | X |
| AEs[d] | X | X | X | X | X | X | X | X | X |
| Medication use | X | X | X | X | X | X | X | X | X |

[a]Hematology includes CBC count, differentials, and platelets.
[b]Blood chemistries include: 1) liver function tests: ALT/SGPT, AST/SGOT, total bilirubin, alkaline phosphatase, albumin, and total protein, 2) renal function tests: creatinine and BUN, and 3) electrolytes: calcium, potassium, sodium, and chloride.
[c]Only females of child-bearing potential will have a pregnancy test. A serum pregnancy test will be performed at the start of screening and a urine pregnancy test will be performed within 7 days prior to the start of treatment.
[d]AEs will be assessed at each study visit before any study procedures are performed as well as after study procedures are performed.

Formulation and Preparation:

Fresh colonies of CFT073 are grown in LB medium overnight. $10^{10}$ CFU of bacteria are pelleted by centrifugation at 4° C., 6000 rpm for 5 minutes and washed twice with 30 ml of PBS. The pellet is re-suspended in 10 ml 4% formaldehyde and then the bacteria are incubated overnight at 4° C. for inactivation. The inactivated bacteria are pelleted by centrifugation at the same conditions, washed three times in 30 ml PBS, re-suspended in PBS, and brought to a concentration of $10^9$ cells/ml (OD=1, 600 nm). The final product is labeled as CFT-FA (formaldehyde inactivated UPEC CFT073).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of treating bladder cancer, the method comprising using a catheter for intravesicularly administering to a subject in need thereof an inactivated pathogenic *E. coli* strain.

2. The method of claim 1, wherein the pathogenic *E. coli* is uropathogenic *E. coli* (UPEC) or enteropathogenic *E. coli* (EPEC).

3. The method of claim 1, wherein the pathogenic *Escherichia coli* is an *Escherichia coli* CFT073 strain.

4. The method of claim 1, wherein the *E. coli* strain has type I fimbria.

5. The method of claim 1, wherein the pathogenic *E. coli* strain is inactivated by formaldehyde.

6. The method of claim 1, wherein said pathogenic *E. coli* is weekly administered.

7. The method of claim 6, wherein said pathogenic *E. coli* is weekly administered in a dosage comprising $10^7$ to $10^{12}$ bacterial cells.

8. The method of claim 1, wherein the *E. coli* strain is administered in combination with an anticancer agent.

9. A method of treating a cancer of the genitourinary system, the method comprising administering to a subject in need thereof a bacterial strain having type I fimbria, the bacterial strain is selected from the group consisting of: (i) an inactivated mutant hemolysin deficient bacterial strain derived from a pathogenic strain of *E. coli*; (ii) an inactivated uropathogenic *Escherichia coli* (UPEC); and (iii) an inactivated enteropathogenic *Escherichia coli* (EPEC), wherein the bacterial strain is intravesicularly administered using a catheter.

10. The method of claim 9 wherein the UPEC or the EPEC is inactivated by formaldehyde.

11. The method of claim 9, wherein the bacterial strain is weekly administered in a dosage comprising $10^7$ to $10^{12}$ bacterial cells.

* * * * *